United States Patent [19]

Miller

[11] Patent Number: 4,917,606
[45] Date of Patent: Apr. 17, 1990

[54] THREADED DENTAL ANCHOR
[75] Inventor: Alan N. Miller, New City, N.Y.
[73] Assignee: IPCO Corporation, White Plains, N.Y.
[21] Appl. No.: 191,347
[22] Filed: May 9, 1988
[51] Int. Cl.[4] .............................................. A61K 5/04
[52] U.S. Cl. ..................................................... 433/225
[58] Field of Search ............... 433/219, 220, 221, 174, 433/225

[56] References Cited

U.S. PATENT DOCUMENTS

| | | | |
|---|---|---|---|
| 2,655,724 | 10/1953 | Brooks | 433/221 |
| 4,053,982 | 10/1977 | Weissman | 433/225 |
| 4,187,611 | 2/1980 | Chan | 433/225 |
| 4,431,416 | 2/1984 | Niznick | 433/174 |
| 4,490,116 | 12/1984 | Deutsch | 433/221 |

Primary Examiner—Gene Mancene
Attorney, Agent, or Firm—Goodman & Teitelbaum

[57] ABSTRACT

A self-threading dental anchor for insertion into a blind channel extending from an excavated surface of a tooth, the channel having a tapered seat portion of predetermined degrees, the dental anchor including an upper retention section to provide retention of a superstructure formed on the tooth, and a lower anchoring section connected thereto for engagement in the tooth channel to threadingly anchor the dental anchor to the tooth, the anchoring section having a helical buttress-type thread thereon. The buttress-type thread has a substantially planar lower surface facing towards a distal insertion end of the anchoring section, and an angled upper surface tapering inwardly towards the upper retention section to provide a crest therebetween, the crest having a knife-like cutting edge. The distal insertion end of the anchoring section is tapered to provide a slope thereon equal to the predetermined degrees of the tapered seat portion of the tooth channel to provide a mating angled configuration therebetween. Preferably, a depth-limiting stop member is disposed between the retention section and the anchoring section. The retention section can have a variety of different configurations, being threaded or unthreaded, for coupling with or within a cooperating driving tool.

33 Claims, 6 Drawing Sheets

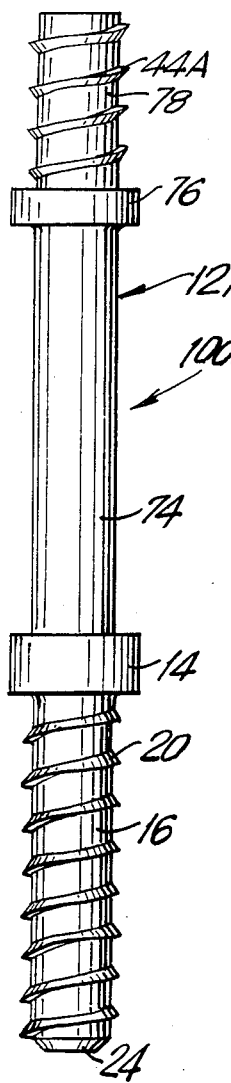
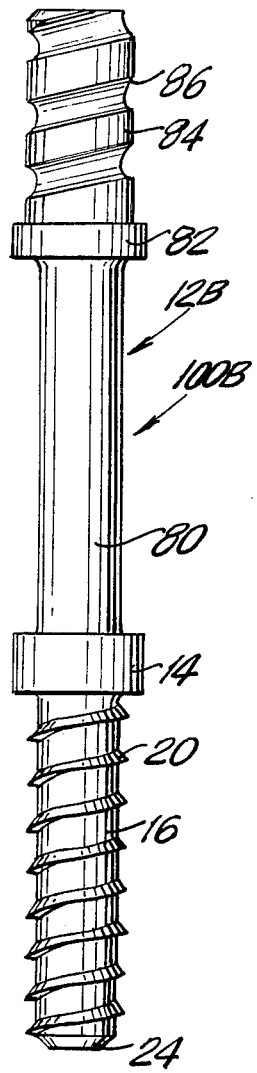
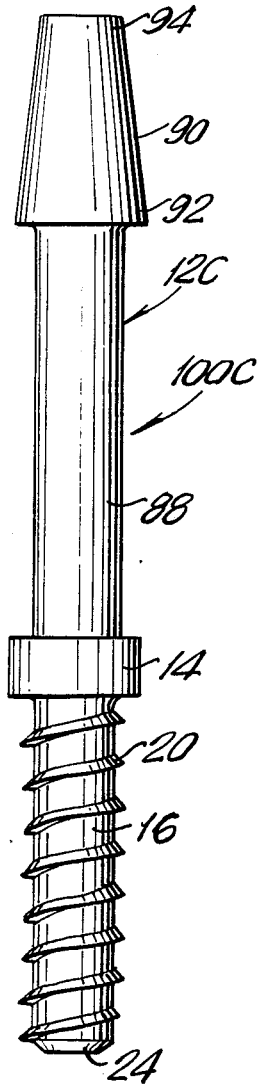
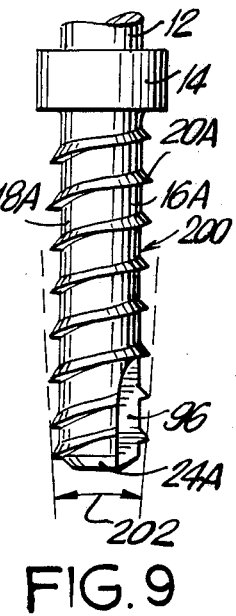
FIG. 6    FIG. 7    FIG. 8
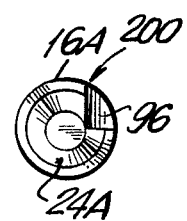
FIG. 9
FIG. 10

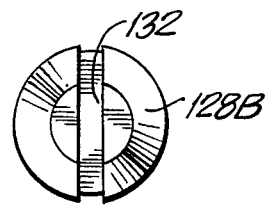
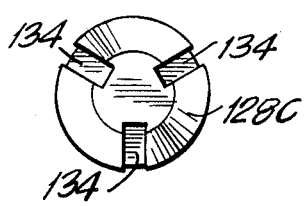
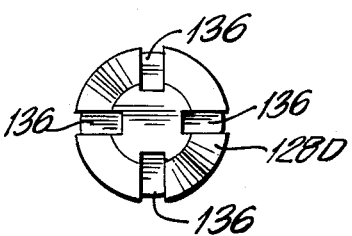
FIG.14  FIG.16  FIG.18
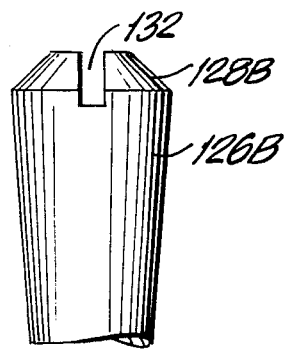
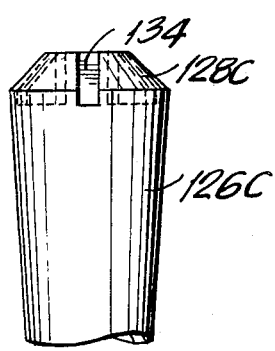
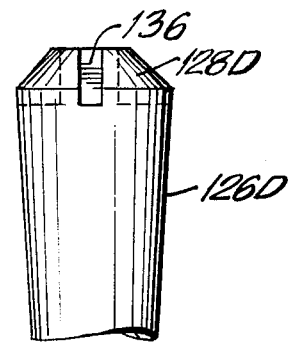
FIG.13  FIG.15  FIG.17
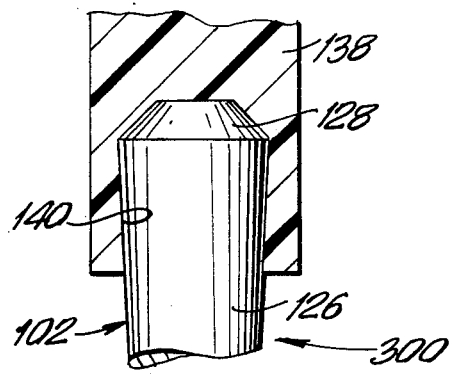
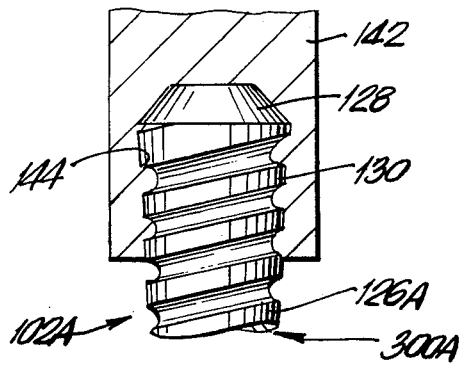
FIG.19  FIG.20
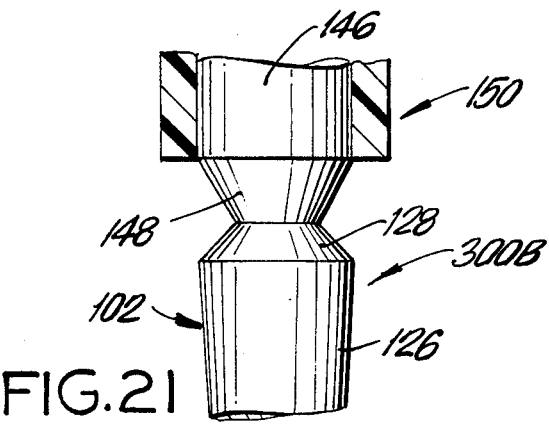
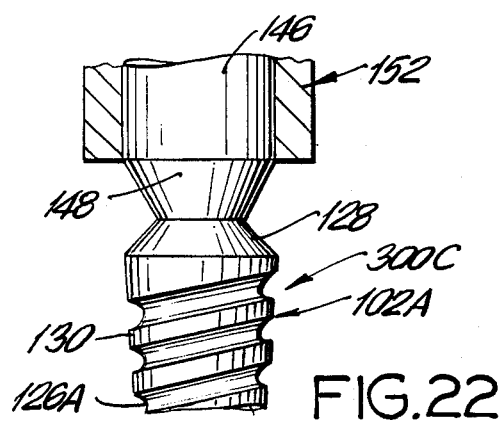
FIG.21  FIG.22

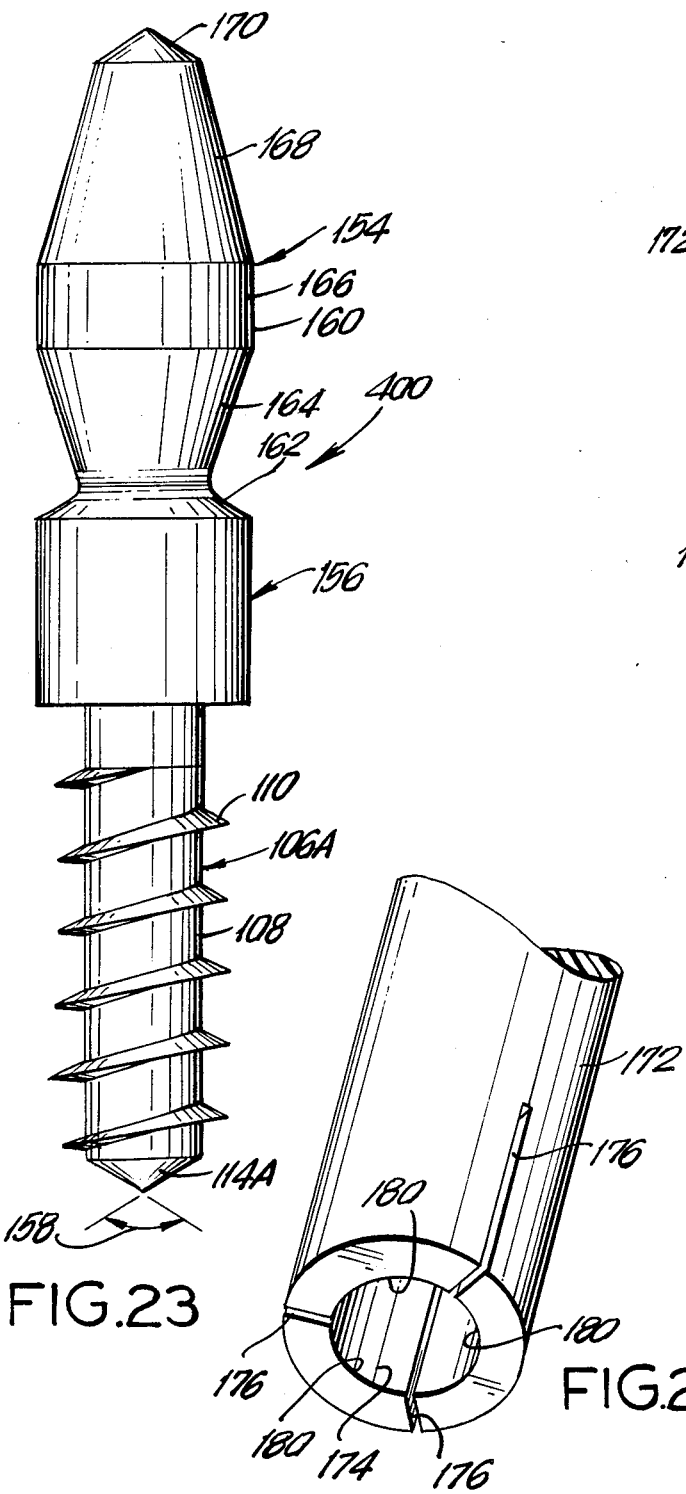
FIG.23
FIG.24
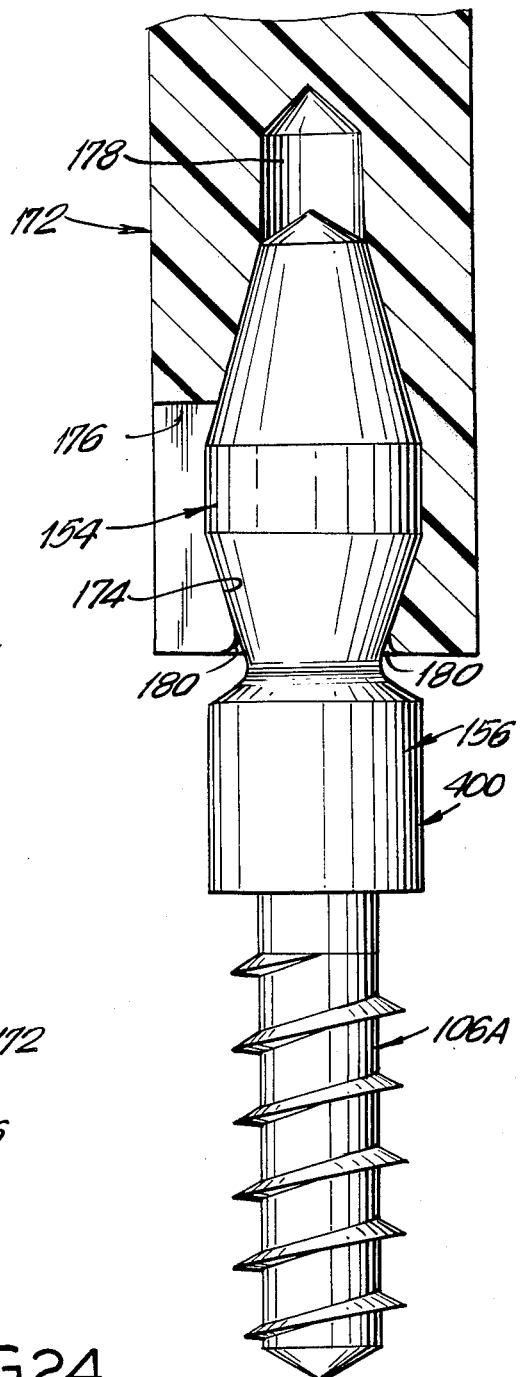
FIG.25

THREADED DENTAL ANCHOR

BACKGROUND OF THE INVENTION

This invention relates generally to dental anchors or pins used for retaining or reinforcing dental restorations, and, more particularly, to a dental anchor having buttress-type threads for the securement thereof in a tooth structure.

Dental anchors or pins for retaining or reinforcing dental restorations are well-known in the dental art, particularly dental anchors having threads thereon for securement in the tooth structure. Usually, such threaded dental anchors are self-threading and have been found to have the greatest retention capabilities when compared to other types of dental anchors or pins.

The most important aspect of using threaded dental anchors is to insure the proper amount of retention thereof, and at the same time to reduce the amount of dentin compression and to eliminate adverse effects upon the surrounding dentin. In the application of threaded dental anchors, it is essential that the practitioner avoid the generation of possible stress upon the dentition during the process of installing the threaded dental anchor into the tooth structure. Improperly inserted threaded dental anchors may result in crazing or cracking of the tooth structure, or at the least generate undesirable stresses on the existing dentin, especially at the blind end or bottom seat portion of the channel formed therefor in the tooth structure when the threaded dental anchor is fully inserted into the channel.

Buttress-type threads are well known in the screw art. However, the assignee of this application has recently discovered that buttress-type threads are extremely useful in the dental art for superb retention thereof in the tooth structure and also for rapid insertion thereof in the tooth structure causing minimal dentin displacement therein. The assignee's co-pending Ser. No. 06/517,006, now U.S. Pat. No. 4,767,332, discloses a dental anchor having a buttress-type thread thereon, where this buttress-type thread has the same structure as that used in the screw art, including a substantially planar upper surface facing away from the insertion end of the dental anchor, an angled or beveled lower surface tapering inwardly towards the insertion end of the dental anchor, and a flattened crest portion disposed between the planar upper surface and angled lower surface. This construction is what one skilled in the art normally assumes when refering to a buttress-type thread.

Though the above dental anchor structure having the buttress-type threads thereon has been proven quite useful in the dental art, the buttress-type thread structure of the present invention has been found to be superior thereto.

SUMMARY OF THE INVENTION

The buttress-type threads on the dental anchor of the present invention increases the retention capabilities of the dental anchor while reducing the dental stresses in the surrounding dental structure.

Accordingly, it is an object of the present invention to provide a dental anchor which avoids the problems of the prior art dental anchors or pins.

A further object of the present invention is to provide a dental anchor having buttress-type threads which provide superior results compared with self-threading dental anchors or pins of the prior art.

A further object of the present invention is to provide a self-threading dental anchor pin having buttress-type threads which contains less threads per inch than the prior art conventional threaded dental anchors or pins.

Yet a further object of the present invention is to provide a dental anchor having buttress-type threads which provides improved holding power and reduces the amount of dentin damage during insertion.

Still another object of the present invention is to provide a dental anchor having a unique buttress-type thread which provides improvements over prior art dental anchors or pins.

Another object of the present invention is to provide a dental anchor having a pilot or distal insertion end which has a mating angled configuration similar to the blind end or bottom seat portion of the channel, which is formed in the tooth structure to receive the dental anchor, to avoid the possibilities of stresses or cracks forming in the understructure, particularly at the seat portion of the channel.

Still yet another object of the present invention is to provide a dental anchor having a unique head portion thereon for securement in the superstructure formed on the tooth structure.

And yet another object of the present invention is to provide a dental anchor as described above which is provided with a tool for inserting the dental anchor into the tooth channel.

Briefly, the present invention is directed to a self-threading dental anchor or pin having a head portion or proximal end provided with means for permitting coupling thereof to a cooperating driving tool to insert the dental anchor into a channel provided in a tooth structure. A shank portion extends from the head portion or proximal end, and has a plurality of buttress-type threads thereon, where the buttress-type threads include a substantially planar lower surface facing towards the insertion, pilot or distal end of the shank portion, and an angled or beveled upper surface tapering inwardly towards the head portion of the dental anchor, and a knife-like cutting edge disposed between the planar lower surface and the angled upper surface to define the crest of the thread. The insertion, pilot or distal end of the shank portion is angled or beveled inwardly towards the end thereof to have a mating angled configuration similar to the blind end or bottom seat portion of the channel formed in the tooth structure. Preferably, a depth-limiting portion is provided between the head portion and the shank portion to limit the depth of insertion of the dental anchor into the channel. The head portion can have a variety of different configurations, being threaded or unthreaded, for coupling with or within a cooperating driving tool.

BRIEF DESCRIPTION OF THE DRAWINGS

With the above and additional objects and advantages in view, as will hereinafter appear, this invention comprises the devices, combinations and arrangements of parts hereinafter described by way of example, and illustrated in the accompanying drawings of preferred embodiments, in which:

FIGS. 6, 7 and 8 are elevational views showing modified dental anchors having buttress-type threads thereon in accordance with the present invention;

FIG. 9 is a fragmented elevational view showing a further modified dental anchor having a buttress-type thread thereon for cutting threads in the tooth channel in accordance with the present invention;

FIG. 10 is a bottom plan view showing the distal end of the dental anchor of FIG. 9;

FIGS. 13, 15 and 17 are fragmented elevational views showing modified head portions of the dental anchor of FIG. 11;

FIGS. 14, 16 and 18 show top plan views of the head portions of FIGS. 13, 15 and 17, respectively;

FIG. 19 shows fragmented elevational view of a tool engaging the head portion of the dental anchor of FIG. 11;

FIG. 20 shows a fragmented elevational view of a tool engaging the head portion of the dental anchor of FIG. 12;

FIG. 21 is a fragmented elevational view showing a tool engaging a modified head portion of the dental anchor shown in FIG. 11;

FIG. 22 is a fragmented elevational view showing a dental tool engaging a modified head portion of the dental anchor shown FIG. 12;

FIG. 23 is an elevational view of yet a still further modified dental tool having buttress-type threads thereon in accordance with the present invention;

FIG. 24 is a fragmented perspective view showing a tool for a dental anchor of FIG. 23; and FIGS. 25 is a fragmented elevational view, partly in cross-section, showing the tool of FIG. 24 engaging the dental anchor of FIG. 23.

In the various figures of the drawings, like reference characters designate like parts.

DETAILED DESCRIPTION OF THE PREFERRED EMBODIMENTS

Figure 1:
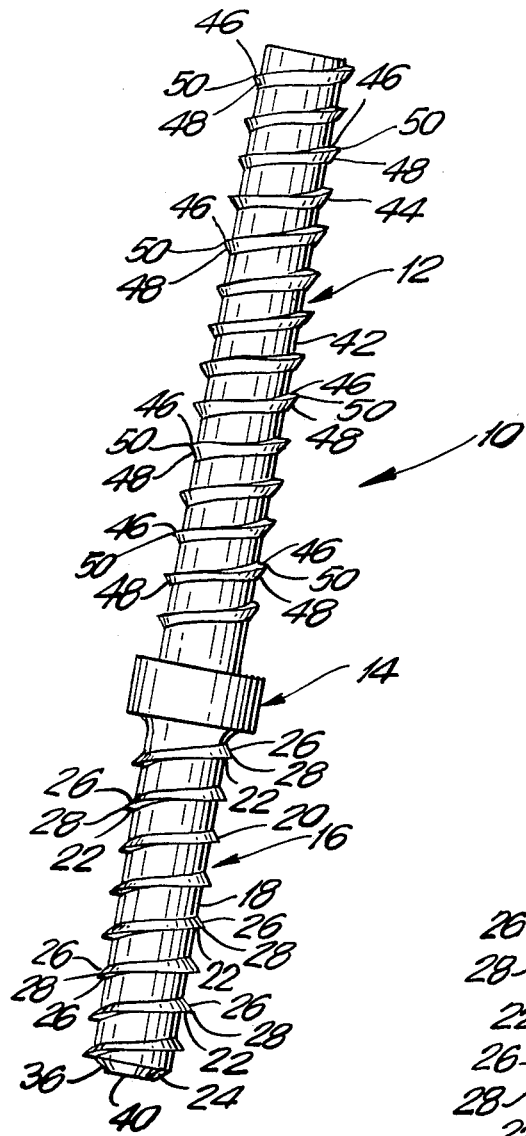
FIG. 1 is a perspective view illustrating a dental anchor having buttress-type threads thereon in accordance with one embodiment of the present invention.

Referring now to the drawings, FIG. 1 shows a dental anchor 10 according to one embodiment of the present invention. The dental anchor 10 includes an upper head or proximal end to define a retention section 12, an intermediate stop member 14, and a lower anchoring section 16. As set forth below, the anchoring section 16 is received in a channel formed in the understructure of a tooth or dentition to anchor the dental anchor to the tooth. The stop member 14 limits the depth of insertion of the dental anchor into the channel so that the retention section 12 extends outwardly from the exposed excavated surface of the tooth to provide retention of a superstructure formed on the tooth.

The anchoring section 16 has an elongated cylindrical body 18 provided with a helical buttress-type thread 20 thereon. The buttress-type thread 20 has a substantially planar lower surface 22 facing towards the insertion, pilot or distal end 24 of the anchoring section 16, as best shown in the enlarged view of FIG. 2, and an angled or beveled upper surface 26 tapering inwardly towards the supper retention section 12 of the dental anchor 10. A knife-like cutting edge is disposed between the planar lower surface 22 and the angled upper surface 26 to define the crest 28 of the buttress-type thread 20.

The minor diameter of the buttress-type thread 20 of the anchoring section 16 is approximately 0.019 inches, which is similar to the minor diameter of prior art dental anchors. However, the major diameter as measured from the crest 28 of the thread 20 is approximately 0.028 inches which is substantially greater than the major diameter of conventional prior art dental anchors for improved retention thereof. The threads per inch are in the range of 62–84, wherein 62 threads per inch is preferred which provides a pitch of approximately 0.016 inches. Therefore, with the anchoring section 16 having a preferred length of approximately 0.087 inches, there will be approximately 5–6 threads on the anchoring section 16 in the preferred embodiment thereof. It should be appreciated, that at the upper end of the range of threads per inch, at 84 threads per inch, the anchoring section 16 would have a smaller pitch of approximately 0.012 inches, and approximately 7–8 threads thereon, as indicated in FIG. 1.

Figure 2:
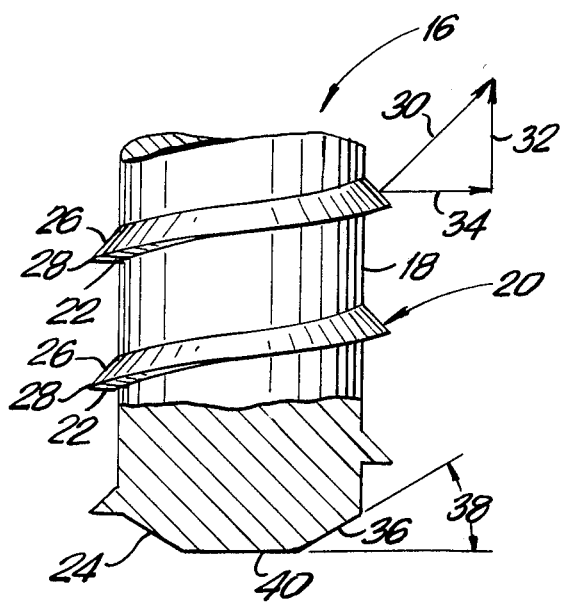
FIG. 2 is a fragmented elevational view, partly in cross-section, showing the distal end portion of the dental anchor of FIG. 1.

The reverse construction of the buttress-type thread 20, where the angled surface 26 tapers inwardly towards the upper retention section 12 of the dental anchor 10, is an important feature of the present invention. As shown in FIG. 2, the resultant vector force 30 which is disposed perpendicular to the angled surface 26, has a vertical vector force 32 and a horizontal vector force 34. Therefore, the force required to pull the dental anchor out from the channel formed in the tooth is increased over the prior art, where now in addition to the normal vertical force required, such as vector force 32, there is an additional horizontal force required, such as vector force 34. Thus, the reverse construction of the buttress-type thread 20 of the present invention increases the retention of the anchoring section 16 within the channel of the tooth over the prior art, by requiring an additional horizontal force which is not present in a conventional prior art buttress-type thread.

Another important feature of the present invention is that the insertion, pilot or distal end 24 of the anchoring section 16 is chamfered or tapered at 36 to provide a slope 38 of approximately 30 degrees as measured from a plan passing along the bottom 40 of the distal end 24. Accordingly, this 30 degree slope 38 is similar to the angle on the end of the drill bit used to form the channel in the tooth, as set forth below, so that the distal end 24 is angled at 36 inwardly towards the end 40 thereof to have a mating angled configuration similar to the blind end or bottom seat portion of the channel formed in the tooth, as set forth below.

The upper retention section 12 also has an elongated cylindrical body 42 provided with a helical buttress-type thread 44 thereon. However, this buttress-type thread 44 is of the conventional type, having a substantially planar upper surface 46 facing away from the insertion, pilot or distal end 24 of the anchoring section 16, and an angled or beveled lower surface 48 tapering inwardly towards the lower anchoring section 16. Again, a knife-like cutter edge is disposed between the planar upper surface 46 and the angled lower surface 48 to define the crest 50 of the buttress-type thread 44. Preferably, the cylindrical body 42 of the retention section 12 has the same diameter as the cylindrical body 18 of the anchoring section 16, so that the minor diameter of the buttress-type thread 44 is approximately 0.019 inches which is the same as the minor diameter of the buttress-type thread 20. Additionally, the major diameter of the buttress-type thread 44 is approximately 0.028 inches which is the same as the major diameter of the buttress-type thread 20, mentioned above. The retention section 12 has a length of approximately 0.160 inches, with the buttress-type thread 44 having a pitch of approximately 0.016 inches in the preferred embodiment, with the smallest pitch being approximately 0.012 inches, the same as the buttress-type thread 20, so that there are approximately ten to fourteen threads on the retention section 12.

It is noted, that the buttress-type thread 44 of the retention section 12 has a reverse construction from the buttress-type thread 20 of the anchoring section 16, and therefore the force required to pull the superstructure off from the retention section 12 is increased over the prior art in the manner as mentioned above with respect to the resultant vector force 30, where now in addition to the normal vertical force required, there is an additional horizontal force required. Thus, the construction of the buttress-type thread 44 of the present invention increases the retention capabilities of the retention section 12 within the superstructure over the prior art, by requiring an additional horizontal force which is not present in prior art conventional screw threads.

The intermediate stop member 14 also has a cylindrical body with a preferred diameter of approximately 0.032 inches so that it is larger than either of the cylindrical bodies 18, 42 of the anchoring section 16 and retention section 12, respectively. The stop member 14 has a height of approximately 0.015 inches in the direction of the longitudinal axis of the dental anchor 10.

Figure 3:
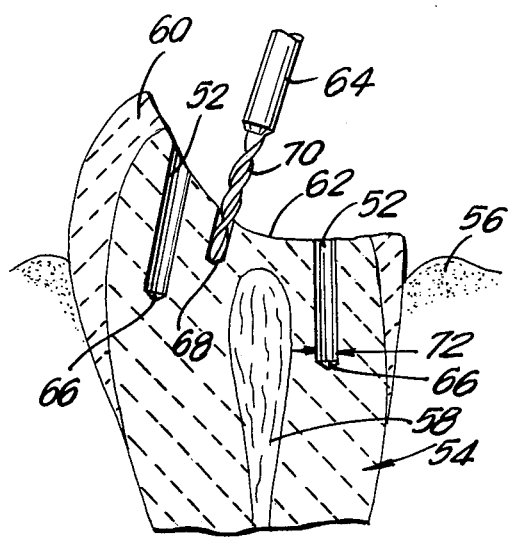
FIG. 3 is an elevational view, partly in cross-section, showing channels being formed in a tooth or dentition with its surface excavated prior to building a superstructure thereon.

FIG. 3 illustrates the channels 52 being formed in the dentin or tooth 54 positioned in the soft tissue or gingiva 56 of the human gum. The tooth 54 includes a pulp channel 58, and is covered by a layer of enamel 60. In order to prepare the tooth 54 for building a superstructure thereon, a portion of the enamel 60 and a portion of the dentin is excavated to remove the decay and the undermined tooth structure so as to provide an excavated surface 62 with the decay removed.

As shown, a conventional spiral drill 64 is urged into the dentin in a conventional manner to form the channels 52, with each channel 52 having a seat portion 66. As mentioned above, the angle on the end 68 of the drill bit 70 of the drill 64 has a 30 degree slope similar to the slope 38 on the distal end 24 of anchoring section 16 so that the blind end or bottom seat portion 66 of the channel 52 has a mating angled configuration similar to the distal end 24 of the anchoring section 16. Furthermore, the dimension 72 representing the major diameter of the drilled channel 52 is less than the major diameter of the anchoring section 16, so that the dental anchor 10 can be self-threaded into the channel 52. Accordingly, the major diameter 72 of the channel 52 is also less than the diameter of the stop member 14 of the dental anchor 10 to limit the insertion of the dental anchor 10 into the channel 52. It is further noted, that the depth of each channel 52 is preferably greater than the length of the anchoring section 16, for the reason set forth below.

Figure 4:
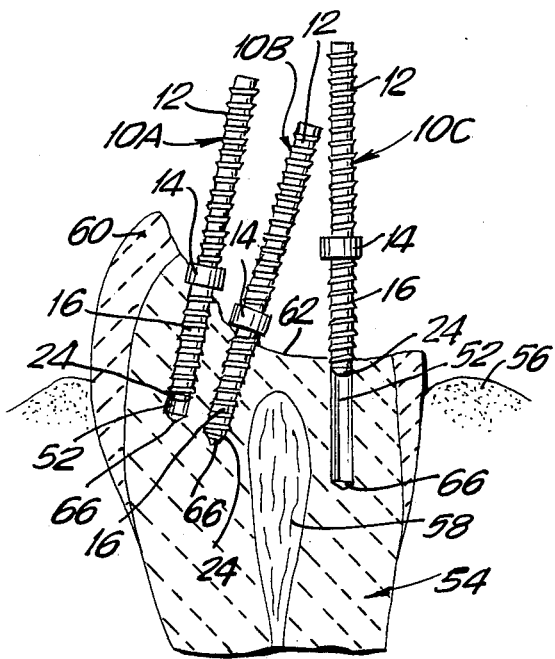
FIG. 4 is an elevational view, partly in cross-section, illustrating the dental anchor of FIG. 1 being inserted into the tooth of FIG. 3.

Referring to FIG. 4, the insertion of the dental anchors into the channels of the tooth will not be described, whereby the insertion of other modified dental anchors set forth below would be the same and, therefore, a further explanation thereof below is not thought necessary. It is noted, that the dental anchors can be rotated into the channels either by a manual tool or a power tool attached or secured to the retention section 12, examples of which are set forth below.

Figure 5:
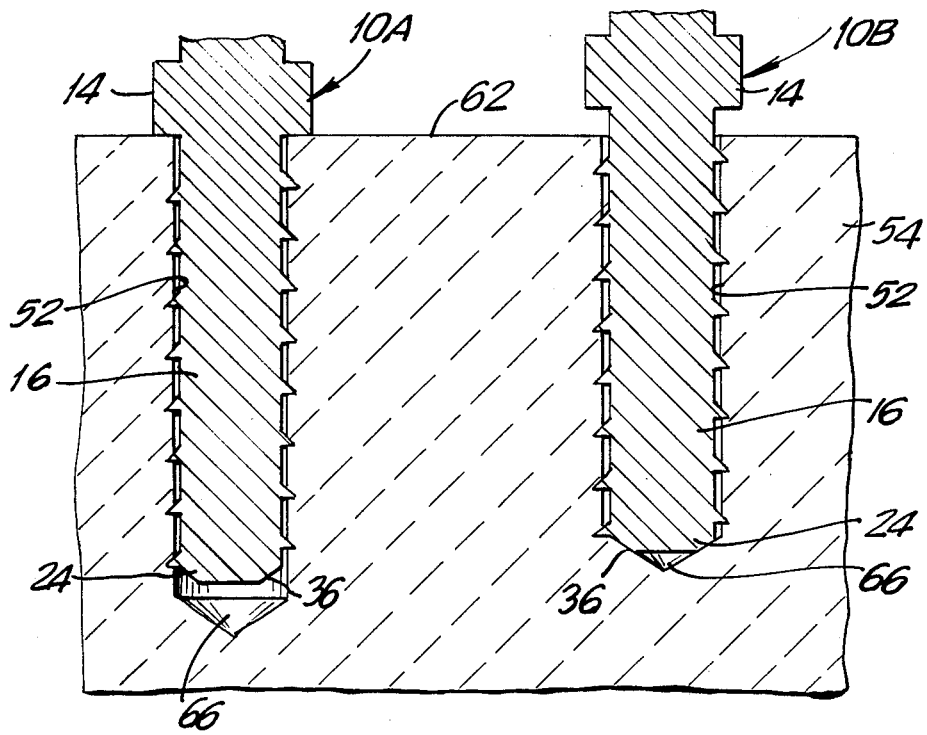
FIG. 5 is an enlarged elevational view in cross-section, comparing the inserted dental anchors of FIG. 4.

FIG. 4 shows two dental anchors 10A and 10B inserted into the channels 52 provided in the tooth 54, and a third dental anchor 10C being inserted into a third channel 52. It is noted, that the stop member 14 of the dental anchor 10A engages the perimeter of the mouth of the channel 52 when the dental anchor 10A is self-threaded therein, so that the insertion operation of the dental anchor 10A is terminated by the stop member 14. Accordingly, the distal end 24 of the dental anchor 10A does not reach the seat portion 66 of the channel 52, as best shown in FIG. 5, wherein the depth length of the channel 52 is longer than the distance between the distal end 24 and the stop member 14 of the dental anchor 10A. Thus, the stress at the seat portion 66 of the channel 52 is substantially reduced, or eliminated, due to the fact that the distal end 24 of the dental anchor 10A does not reach or engage the seat portion 66 because of the engagement of the stop member 14 of the dental anchor 10A. Additionaly, if the upper retention section 12 of the dental anchor 10A is bent or cut after insertion thereof, which is customary in the dental anchor art before the superstructure is formed on the tooth, there obviously will be minimal or no stress produced at the seat portion 66 of the channel 52 receivng the dental anchor 10A.

However, in the case of dental anchor 10B, the channel 52 has a depth length less than the distance between the distal end 24 and the stop member 14 of the dental anchor 10B, as best shown in FIG. 5. In this case, the stop member 14 of dental anchor 10B will not engage the perimeter of the mouth of the channel 52, but rather the distal end 24 of the dental anchor 10B will bottom-out against the seat portion 66 of the channel 52. However, because the blind end or bottom seat portion 66 of the channel 52 has a mating angled configuration similar to the chamfer 36 of the distal end 24 of the anchoring section 16 of the dental anchor 10B, the stress at the seat portion 66 of the channel 52 will be substantially reduced even though engagement is made between the dental anchor 10B and the seat portion 66.

FIGS. 6, 7 and 8 show embodiments of modified dental anchors 100A, 100B and 100C, where it is noted that in each of these modified dental anchors, the intermediate stop member 14 and the lower anchoring section 16 has the same construction as the above-mentioned stop member 14 and anchoring section 16 of the dental anchor 10. Accordingly, in these three embodiments, only the upper retention section has been modified, where in some cases these modified retention sections of dental anchors 100A, 100B and 100C will provide a better retention of the superstructure than the above-mentioned retention section 12 of the dental anchor 10, it being noted that the cylindrical portion of each of the modified retention sections is easier to bend or cut after insertion of the dental anchor into the tooth, as mentioned above.

FIG. 6 shows dental anchor 100A having a modified retention section 12A including a cylindrical portion 74 having its lower end connected to the stop member 14, and its upper end connected to a collar 76. The cylindrical portion 74 has the same diameter as the minor diameter of the anchoring section 16, and the collar 76 has the same diameter as the stop member 14. An upper portion 78 having conventional buttress-type threads 44A thereon is connected to the upper end of the collar 76, where the upper portion 78 has the same construction as the retention section 12 of the dental anchor 10, but being shorter in the longitudinal length thereof. Preferably, the cylindrical portion 74 has an axial length of 0.100 inches, the collar 76 has an axial length of 0.010 inches, and the upper portion 78 has an axial length of 0.050 inches.

FIG. 7 shows dental anchor 100B having a modified retention section 12B including a cylindrical portion 80 having its lower end connected to the stop member 14, and its upper end connected to a collar 82. The cylindrical portion 80 has the same diameter as the minor diameter of the anchoring section 16, and the collar 82 has the same diameter as the stop member 14. An upper portion 84 having a conventional screw thread 86 thereon is connected to the upper end of the collar 82, where the upper portion 84 is similar to the upper portion 78 of the dental anchor 100A, but is slightly longer in the longitudinal length thereof. Preferably, the clindrical portion 80 has an axial length of 0.090 inches, the collar 82 has an axial length of 0.010 inches, and the threaded upper portion 84 has an axial length of 0.060 inches.

FIG. 8 shows dental anchor 100C having a modified retention section 12C including a cylindrical portion 88 having its lower end connected to the stop member 14, and its upper end connected to a shoulder member 90. The cylindrical portion 88 has the same diameter as the minor diameter of the anchoring section 16. The shoulder 90 is cylindrical and tapers from its widest lower end 92, which has the same diameter as the stop member 14 inwardly to its narrowest upper free end 94, which has a diameter equal to the diameter of the cylindrical portion 88. Preferably, the cylindrical portion 88 has an axial length of 0.100 inches, and the should 90 has an axial length of 0.060 inches.

It is noted, that each of the above-mentioned self-threading anchoring sections are of the thread-forming type, where the dentin of the tooth 54 is compressed as the threads of the anchoring sections are forced into the side walls of the channel 52. Accordingly, FIG. 9 shows a modified anchoring section 16A of dental anchor 200 which is of the thread-cutting type. The cylindrical body 18A is tapered at the lower free end thereof, there being preferably an approximately ten degree taper thereon, as indicated by the arrows 202, to facilitate insertion into the tooth channel 52. Again, the cylindrical body is provided with a helical buttress-type thread 20A thereon, being the cutting type which is known in the dental art. Additionally, a longitudinally extending cutout or notch 96 is provided in the tapered lower end portion of the cylindrical body 18A, as shown in FIGS. 9 and 10, to provide space for the dentin which is cut as the anchoring section 16A is being self-threaded into the channel 52. The notch 96 extends through the distal end 24A of the anchoring section 16A. The stop member 14 and retention section 12 of the dental anchor 200 can be similar to any one shown on the previously above-mentioned dental anchors.

Figure 11:
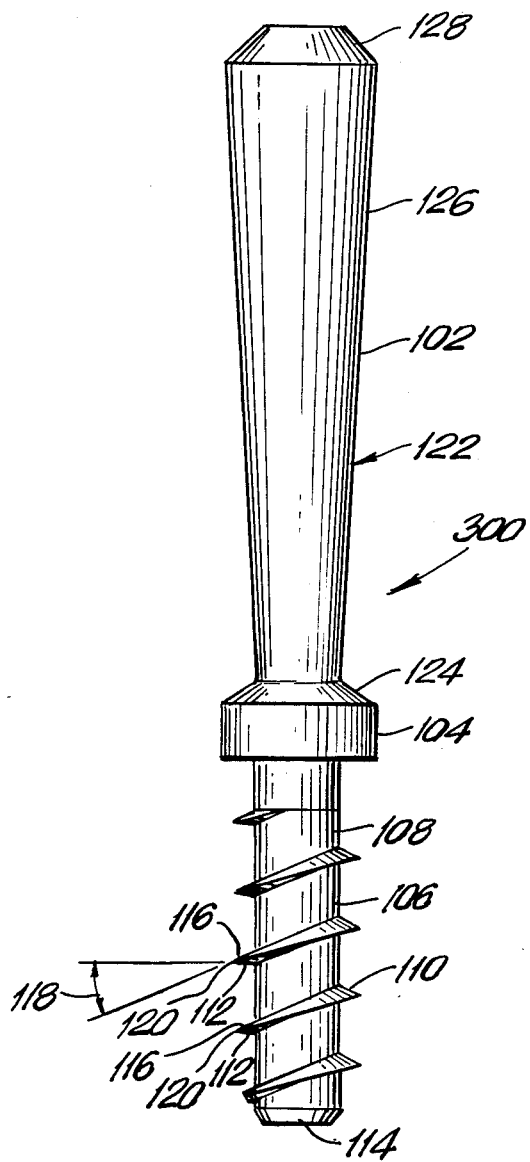
FIGS. 11 and 12 are elevational views showing still further modified dental anchors having buttress-type threads thereon in accordance with the present invention.

FIG. 11 shows an embodiment of a still further modified dental anchor 300 including a retention section 102, an intermediate stop member 104, and a lower anchoring section 106. Here again, the anchoring section 106 includes a cylindrical body 108 provided with a helical buttress-type thread 110 thereon. The buttress-type thread 110 is reversed to be similar to the above-mentioned buttress-type thread 20 of the dental anchor 10. However, the planar lower surface 112 of buttress-type thread 110 facing towards the distal end 114 and the angled upper surface 116 tapering inwardly away from the distal end 114 have a smaller acute angle 118 therebetween, preferably 25 degrees, to reduce the thickness of the buttress-type thread 110 and to make the knife-like cutting edge or crest 120 therebetween sharper in construction. Thus, the buttress-type thread 110 compresses less dentin of the tooth channel 52 when being inserted therein, causing less stresses during the insertion, while still retaining the same anchoring capabilities in the dentin of the tooth 54. Here again, the minor diameter of the buttress-type thread 110 is still approximately 0.019 inches and the major diameter is still approximately 0.028 inches. The anchoring section 106 has a length of approximately 0.080 inches, where the threads per inch and pitch are the same as mentioned above with respect to the anchoring section 16 of the dental anchor 10. It is noted, that the distal end 114 is the same as the distal end 24 of the above-mentioned anchoring section 16.

The intermediate stop member 104 is similar to the above-mentioned stop member 14, having a cylindrical body with a preferred diameter of aproximately 0.034 inches so that it is larger than the cylindrical body 108 of the anchoring section 106. The stop member 104 has a height of approximately 0.010 inches in the direction of the longitudinal axis of the dental anchor 300.

The upper retention section 102 has a cylindrical body 122 including a small lower tapered portion 124, an elongated intermediate tapered portion 126, and a chamfered or beveled top end portion 128. The lower portion 124 necks down inwardly from the stop member 104 to a diameter approximately equal to the diameter of the minor diameter of the anchoring section 106, at which point it is connected to the lower end of the intermediate portion 126. The intermediate portion 126 tapers upwardly and outwardly to its widest part at the top end thereof, which is approximately equal to the diameter of the stop member 104, at which point it is connected to the top end portion 128. The upper retention section 102 has a length of approximately 0.150 inches.

Figure 12:
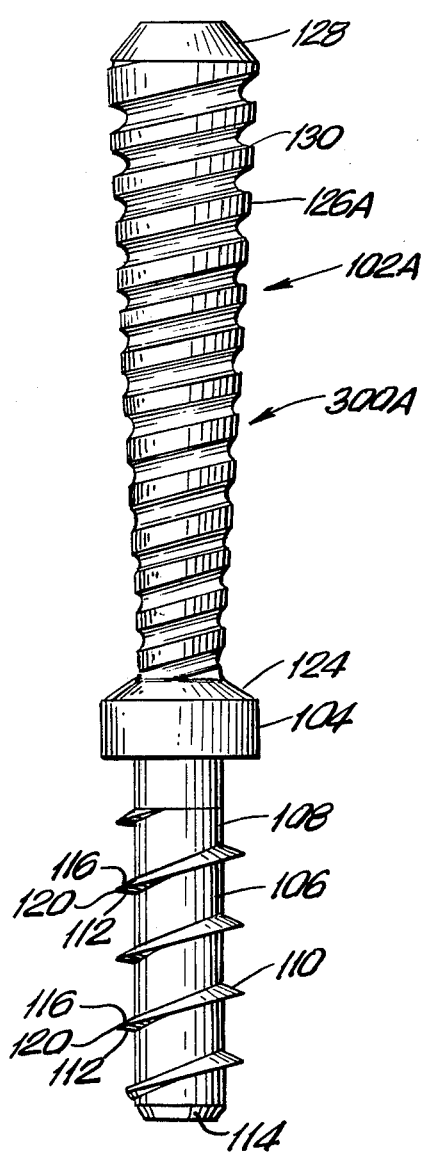

FIG. 12 shows a further embodiment of a modified dental anchor 300A, which is the same as the above-mentioned dental anchor 300 except for the intermediate tapered portion 126A of the retention section 102. Accordingly, the intermediate tapered portion 126A of the retention section 102A is provided with a conventional screw thread 130 thereabout. Obviously, if desired, the intermediate tapered portion 126A could be provided with a buttress-type thread in the manner mentioned above.

FIGS. 13–18 show modifications of the head portion of the retention section of the dental anchor 300. FIGS. 13 and 14 show a slot 132 extending across the top end portion 126B of the retention section of the dental anchor. Accordingly, the slot 132 receives a screwdriver-like blade of a tool therein to rotate the dental anchor for a threaded engagement in the channel 52 of the tooth 54.

FIGS. 15 and 16 show three spaced-apart slots 134, approximately 120 degrees apart, provided in the top end portion 128C and extending into a part of the intermediate tapered portion 126C. Accordingly, here again, the slots 134 receive mating projections on a tool for rotating the dental anchor for a threaded engagement in the channel 52 of the tooth 54.

Furthermore, FIGS. 17 and 18 show four spaced-apart slots 136, approximately 90 degrees apart, provided in the top end portion 128D and extending into a part of the intermediate tapered portion 126D. Accordingly, here again, the slots 136 receive mating projections on a tool for rotating the dental anchor for a threaded engagement in the channel 52 of the tooth 54.

FIG. 19 shows a lower portion of a tool 138, either a manual tool or a power tool, having an opening 140 in the end thereof matingly receiving the upper end of the intermediate portion 126 and the top end portion 128 of the retention section 102 of the dental anchor 300 in order to rotate the dental anchor 300 for threaded engagement in the channel 52 of the tooth 54. Preferably, the tool 138 is fabricated from a plastic material.

FIG. 20 shows a lower portion of another tool 142, also either a manual tool or a power tool, having athreaded opening 144 in the end thereof to matingly thread onto the upper end of the intermediate portion 126A of the retention section 102A of the dental anchor 300A in order to rotate the dental anchor 300A for threaded engagement in the channel 52 of the tooth 54. Provision is made in the opening 144 to receive the top end portion 128. Preferably the tool 142 is from a metal material.

FIGS. 21 and 22 show embodiments of a modified dental anchor 300B similar to dental anchor 300, and a modified dental anchor 300C similar to dental anchor 300A, respectively. The dental anchors 300B, 300C each are provided with a manipulating end section 146 thereon having a necked-down reduced portion 148 connected at its smallest diameter to the top end portion 128 of each dental anchor 300B, 300C to extend along the longitudinal axis thereof. Such a manipulating end section 146 is well known in the art, and can have many different structural configurations. A tool 150 preferably plastic as shown in FIG. 21, or a tool 152 preferably metal as shown in FIG. 22, engages the manipulating end section 146 in order to rotate the dental anchor 300B, 300C for threaded engagement in the channel 52 of the tooth 54. Once the stop member 104 engages the tooth 54, or the distal end 114 engages the bottom of the seat portion 66 of the channel 52, the insertion of the dental anchor 300B, 300C is completed, at which time due to the frictional resistance of further rotations of the dental anchor 300B, 300C, the reduced portion 148 will shear off from the top end portion 128 of the dental anchor 300B, 300C, as is well known in the dental art.

FIG. 23 shows an embodiment of yet still a further modified dental anchor 400 including a retention section 154, and intermediate stop member 156, and a lower anchoring section 106A. The anchoring section 106A is similar to the above-mentioned anchoring section 106 of the dental anchor 300, having a cylindrical body 108 and a helical buttress-type thread 110 thereon. The only change is that the distal end 114A is conically shaped to provide an angle 158 of approximately 120 degrees, so that the angled side of the distal end 114A still has a slope of 30 degrees similar to the above-mentioned distal end 114 of the dental anchor 300 in order to be matingly received in the seat portion 66 of the channel 52 as mentioned above. The anchoring section 106A has the same dimensions as the anchoring section 106 of the dental anchor 300, except the preferred actual axial length thereof is slightly less at approximately 0.078 inches.

The intermediate stop member 156 has a cylindrical body with a preferred diameter of approximately 0.0348 inches so that it is larger than the cylindrical body 108 of the anchoring section 106A. The stop member 156 has a height of approximately 0.030 inches in the direction of the longitudinal axis of the dental anchor 400.

The upper retention section 154 has a cylindrical body 160 including a small lower tapered portion 162, a first lower intermediate tapered portion 164, a central cylindrical portion 166, a second upper intermediate portion 168, and a conical top end portion 170. The lower portion 162 necks down inwardly from the stop member 156 to a diameter approximately equal to the diameter of the minor diameter of the anchoring section 106A, at which point it is connected to the lower end of the first intermediate portion 164. The first intermediate portion 164 tapers upwardly and outwardly to its widest part at the top end thereof which is approximately equal to the diameter of the stop member 156, at which point it is connected to the cylindrical portion 166 having a diameter approximately equal to the stop member 156. The cylindrical portion 166 is connected at its top end to the second intermediate portion 168 which tapers upwardly and inwardly to its narrow part at the top end thereof, which is approximately equal to the diameter of minor diameter of the anchoring section 106A, at which point it is connected to the top conical portion 170. The upper retention section 154 has a length of approximately 0.082 inches.

FIG. 24 shows a lower portion of a tool 172, either a manual tool or a power tool, having an opening 174 in the end thereof for matingly receiving the retention section 154 of the dental anchor 400. Spaced apart slots 176, preferably three slots, extend from the periphery of the tool 172 at the end portion thereof to the opening 174 in order to permit expansion of the end portion of the tool 172 over the retention section 154. Preferably, the tool 172 is fabricated from a plastic material as shown.

FIG. 25 shows the tool 172 in its snapped on position on the retention section 154 of the dental anchor 400. FIG. 25 clearly shows that the opening 174 has a mating configuration similar to the shape of the retention section 154. It is noted, that the opening 174 has an inward extension 178 positioned above the conical top portion 170 of the retention section 154 to facilitate the snapping of the tool 172 onto the retention section 154, so that provision is made for the air pressure within the opening 174. It is further noted, that the mouth of the opening 174 is curved at 180 to facilitate the mounting thereof onto the retention section 154.

Numerous alterations of the structures herein disclosed will suggest themselves to those skilled in the art. However, it is to be understood, that the present disclosure relates to preferred embodiments of the invention which are for the purpose of illustration only, and are not to be construed as limitations of the invention.

What is claimed is:

1. A dental anchor for insertion into a blind channel extending from an excavated surface of a tooth, the channel having a tapered seat portion of predetermined degrees, said dental anchor comprising:
- an upper retention section to provide retention of a superstructure formed on the tooth;
- a lower anchoring section connected to said upper retention section;
- said anchoring section including a helical buttress-type thread thereon along its entire length for self-threading engagement in the tooth channel to anchor said dental anchor to the tooth; and
- said buttress-type thread having a substantially planar lower surface facing towards a distal insertion end of said anchoring section, an angled upper surface tapering inwardly towards said upper retention section, and a crest disposed between said planar lower surface and said angled upper surface.

2. A dental anchor according to claim 1, wherein stop menas are disposed between said retention section and said anchoring section for limiting depth of insertion of said dental anchor into the channel so that said distal insertion end is prevented from engaging in the seat portion of the channel.

3. A dental anchor according to claim 1, wherein said thread crest has a knife-like cutting edge.

4. A dental anchor according to claim 3, wherein said knife-like cutting edge has an acute angle of twenty-five degrees.

5. A dental anchor according to claim 3, wherein said buttress-type thread is of a thread-forming type to compress dentin of the tooth.

6. A dental anchor according to claim 3, wherein said buttress-type thread is of a thread-cutting type to cut into dentin of the tooth.

7. A dental anchor according to claim 6, wherein said anchoring section is tapered at a lower free end thereof to facilitate insertion into the tooth channel, said lower free end having a longitudinally extending cutout therein to receive the cut dentin.

8. A dental anchor according to claim 1, wherein said buttress-type thread has a range of 62 to 84 threads per inch.

9. A dental anchor according to claim 8, wherein said buttress-type thread has 62 threads per inch to provide a pitch of approximately 0.016 inches.

10. A dental anchor according to claim 1, wherein said dista-insertion end of said anchoring section is tapered to provide a slope thereon equal to the predetermined degrees of the tapered seat portion of the tooth channel to provide a mating angled configuration therebetween.

11. A dental anchor according to claim 10, wherein said slope of said distal insertion end is thirty degrees.

12. A dental anchor according to claim 1, wherein said upper retention section has a helical thread thereon.

13. A dental anchor according to claim 12, wherein said retention section thread is a buttress-type thread having a substantially planar upper surface facing away from said distal insertion end, and an angled lower surface tapering inwardly towards said lower anchoring section to provide a crest therebetween, so that said retention section thread has a reverse construction relative to said anchoring section thread.

14. A dental anchor according to claim 13, wherein a cylindrical portion is provided on said upper retention s4ction between said retention section thread and said lower anchoring section.

15. A dental anchor according to claim 12, wherein a cylindrical portion is provided on said upper retention section between said retention section thread and said lower anchoring section.

16. A dental anchor according to claim 15, wherein a collar is disposed between said retention section thread and said cylindrical portion, and a stop member is disposed between said cylindrical portion and said lower anchoring section.

17. A dental anchor according to claim 16, wherein said retention section thread is a buttress-type thread.

18. A dental anchor according to claim 1, wherein said retention section includes a first cylindrical portion connected to said anchoring section, and a second cylindrical portion connected to said first cylindrical portion in an axial alignment therewith, said second cylindrical portion being tapered inwardly away from said first cylindrical portion to provide an enlarged shoulder adjacent to said first cylindrical portion, said enlarged shoulder having a larger diameter than said first cylindrical portion.

19. A dental anchor according to claim 18, wherein a stop member is disposed between said first cylindrical portion and said anchoring section.

20. A dental anchor according to claim 1, wherein said retention section includes an elongated cylindrical portion tapering outwardly away from said anchoring section, a top end portion of said cylindrical portion having a larger diameter than said anchoring section.

21. A dental anchor according to claim 20, wherein a stop member is disposed between said cylindrical portion and said anchoring section.

22. A dental anchor according to claim 20, wherein said cylindrical portion has a helical thread thereon.

23. A dental anchor according to claim 1, wherein an upper end of said retention section is provided with slot means therein to receive a tool for rotating said dental anchor into threaded engagement in the tooth channel.

24. A dental anchor according to claim 1, including a manipulating end section connected to said dental anchor, said manipulating end section having a necked-down reduced portion connected at its smallest dimension to a top end portion of said retention section in axial alignment therewith so that said reduced portion shears off from said top end portion when said dental anchor is seated in the tooth channel.

25. A dental anchor according to claim 1 in combination with a tool, said tool having means for rotating said dental anchor into threaded engagement in the tooth channel.

26. A dental anchor in combination with a tool according to claim 25, wherein said tool has an opening in an end thereof to receive said retention section therein.

27. A dental anchor for insertion into a blind channel extending from an excavated surface of a tooth, the channel having a tapered seat portion of predetermined degrees, said dental anchor comprising:
- an upper retention section to provide retention of a superstructure formed on the tooth;
- a lower anchoring section connected to said upper retention section;
- said anchoring section including a helical buttress-type thread thereon for self-threading engagement in the tooth channel to anchor said dental anchor to the tooth;
- said buttress-type thread having a substantially planar lower surface facing towards a distal insertion end of said anchoring section, an angled upper surface tapering inwardly towards said upper retention section, and a crest disposed between said planar lower surface and said angled upper surface; and said upper retention section including a lowest first portion tapering inwardly away from said anchoring section, a second intermediate portion connected to said first portion and tapering outwardly away from said first portion, a third central cylindrical portion connected to said second intermediate portion, a fourth intermediate portion connected to said third central cylindrical portion and tapering inwardly away from said third central cylindrical portion, and a fifth conical top end portion connected to said fourth intermediate portion, all of said retention section portions being in axial alignment with each other.

28. A dental anchor according to claim 27, wherein a stop member is disposed between said anchoring section and said first portion of said retention section.

29. A dental anchor according to claim 27 in combination with a tool, said tool having means for rotating said dental anchor into threaded engagement in the tooth channel, said tool having an opening in an end thereof to recieve said retention section therein.

30. A dental anchor in combination with a tool according to claim 29, wherein said end of said tool is provided with slot means to snap said tool end over said retention section.

31. A dental anchor for insertion into a blind channel extending from an excavated surface of a tooth, said dental anchor comprising:

an upper retention section to provide retention of a superstructure formed on the tooth;

a lower anchoring section connected to said upper retention section;

said anchoring section including means for self-threading engagement in the tooth channel to anchor said dental anchor to the tooth;

stop means being disposed between said retention section and said anchoring section for limiting depth of insertion of said dental anchor into the channel so that a distal insertion end of, said anchoring section is prevented from engaging in a seat portion of the channel;

said stop means including a collar, said collar having a maximum transverse outer dimension equal to a maximum transverse outer dimension of said retention section so that said dental anchor can be manufactured from a stock material having said maximum transvese outer dimension;

said retention section having a necked-down reduced portion connected at its smallest dimension to an upper portion of said collar, said necked-down reduced portion being less than said maximum transverse outer dimensions of said retention section and said collar so that the superstructure can be received in said necked-down reduced portion for retention thereof;

said retention section having an entirely smooth outer surface; and said retention section including a first portion connected to said necked-down reduced portion and tapering outwardly away from said collar, a second central cylindrical portion connected to said first portion, a third portion connected to said second central cylindrical portion and tapering inwardly away from said second central cylindrical portion, and a fourth conical top end portion connected to said third portion, all of said retention section portions being in axial alignment with each other.

32. A dental anchor for insertion into a blind channel extending from an excavated surface of a tooth, said dental anchor comprising:

an upper retention section to provide retention of a superstructure formed on the tooth;

a lower anchoring section connected to said upper retention section;

said anchoring section including means for self-threading engagement in the tooth channel to anchor said dental anchor to the tooth;

stop means being disposed between said retention section and said anchoring section for limiting depth of insertion of said dental anchor into the channel so that a distal insertion end of said anchoring section is prevented from engaging in a seat portion of the channel;

said stop means including a collar, said collar having a maximum transverse outer dimension equal to a maximum transverse outer dimension of said retention section so that said dental anchor can be manufactured from a stock material having said maximum transverse outer dimension;

said retention section having a necked-down reduced portion connected at its smallest dimension to an upper portion of said collar, said necked-down reduced portion being less than said maximum transverse outer dimensions of said retention section and said collar so that the superstructure can be received in said necked-down reduced portion for retention thereof;

said retention section having an entirely smooth outer surface; and said means for self-threading engagement including a helical buttress-type thread having a substantially planar lower surface facing towards said distal insertion end of said anchoring section, an angled upper surface tapering inwardly towards said upper retention section, and a crest disposed between said planar lower surface and said angled upper surface.

33. A dental anchor according to claim 32, wherein said retention section includes an elongated cylindrical portion tapering outwardly away from said collar from said necked-down reduced portion to said maximum transverse outer dimension of said retention section at a top end portion of said cylindrical portion.

* * * * *